(12) United States Patent
Loescher et al.

(10) Patent No.: US 7,825,282 B2
(45) Date of Patent: Nov. 2, 2010

(54) PROCESS FOR THE CONVERSION OF TERTIARY BUTYL ALCOHOL TO ETHYL TERTIARY BUTYL ETHER

(75) Inventors: Mitchell E. Loescher, Houston, TX (US); Lawrence A. Smith, Jr., Pasadena, TX (US)

(73) Assignee: Catalytic Distillation Technologies, Pasadena, TX (US)

( * ) Notice: Subject to any disclaimer, the term of this patent is extended or adjusted under 35 U.S.C. 154(b) by 383 days.

(21) Appl. No.: 11/857,160

(22) Filed: Sep. 18, 2007

(65) Prior Publication Data

US 2009/0076312 A1    Mar. 19, 2009

(51) Int. Cl.
   *C07C 41/09*    (2006.01)
   *B01J 8/02*    (2006.01)
(52) U.S. Cl. ...................... 568/698; 422/192
(58) Field of Classification Search ............. None
   See application file for complete search history.

(56) References Cited

U.S. PATENT DOCUMENTS

| | | | |
|---|---|---|---|
| 3,254,023 A * | 5/1966 | Miale et al. ............ | 208/120.15 |
| 4,334,890 A | 6/1982 | Kochar et al. | |
| 4,423,271 A * | 12/1983 | Obenaus et al. ............ | 585/639 |
| 4,935,552 A | 6/1990 | Child et al. | |
| 5,190,730 A | 3/1993 | Smith, Jr. et al. | |
| 5,231,234 A | 7/1993 | Arganbright et al. | |
| 5,248,836 A | 9/1993 | Bakshi et al. | |
| 5,292,964 A | 3/1994 | Gupta | |
| 5,364,981 A | 11/1994 | Knifton et al. | |
| 5,424,458 A | 6/1995 | Sullivan et al. | |
| 5,449,839 A | 9/1995 | Knifton et al. | |
| 5,527,970 A | 6/1996 | Hwan et al. | |
| 5,621,150 A | 4/1997 | Rastelli et al. | |
| 5,637,777 A | 6/1997 | Aittamaa et al. | |
| 5,716,896 A | 2/1998 | Knifton et al. | |
| 5,811,620 A | 9/1998 | Knifton et al. | |
| 5,849,971 A | 12/1998 | Sakuth et al. | |
| 6,107,526 A | 8/2000 | Frey et al. | |
| 7,223,875 B2 | 5/2007 | Kelly | |

FOREIGN PATENT DOCUMENTS

EP      0 071 032    *   2/1983

OTHER PUBLICATIONS

International Search Report with Written Opinion of the Searching Authorityissued in PCT Application No. US2008/074278, dated Mar. 20, 2009. (9 pages).

* cited by examiner

*Primary Examiner*—Rosalynd Keys
(74) *Attorney, Agent, or Firm*—Osha • Liang LLP

(57) ABSTRACT

A process for the conversion of tertiary butyl alcohol to ethyl tertiary butyl ether, including: dehydrating tertiary butyl alcohol to form a product stream comprising isobutylene and water; separating the product stream to form an isobutylene-rich fraction and a water-rich fraction; separating the water-rich fraction to recover a hydrocarbon fraction and a water fraction having less than 1 ppm hydrocarbon content; reacting isobutylene in the isobutylene-rich fraction with ethanol to form a reaction product comprising ethyl tertiary butyl ether; separating the reaction product to recover unreacted ethanol and an ethyl tertiary butyl ether stream; and recycling at least a portion of the unreacted ethanol to the reacting; wherein the ethyl tertiary butyl ether stream comprises at least 99 weight percent ethyl tertiary butyl ether.

8 Claims, 2 Drawing Sheets

PROCESS FOR THE CONVERSION OF TERTIARY BUTYL ALCOHOL TO ETHYL TERTIARY BUTYL ETHER

BACKGROUND OF DISCLOSURE

1. Field of the Disclosure

Embodiments disclosed herein relate generally to a process for the conversion of tertiary butyl alcohol (TBA) to ethyl tertiary butyl ether (ETBE). More specifically, embodiments disclosed herein relate to the dehydration of TBA to isobutylene, which is subsequently reacted with ethanol to form ETBE.

2. Background

Various commercial processes for the production of propylene oxide include the reaction of propylene with tertiary butyl hydroperoxide, resulting in the formation of propylene oxide and TBA. See, for example, U.S. Pat. Nos. 7,223,875 and 5,424,458.

In order for the propylene oxide process to be economical, a good value for the TBA must be realized. Conversion of the TBA to a high-octane gasoline blendstock may allow for the needed TBA value to be realized.

For example, U.S. Pat. No. 5,424,458 discloses that the TBA can be dehydrated to isobutylene. The isobutylene may then be converted in an existing etherification unit to methyl tertiary butyl ether (MTBE). Alternatively, the TBA may be reacted directly in the etherification unit with methanol to form MTBE in a one-step etherification reaction, such as those disclosed in U.S. Pat. Nos. 5,716,896 and 5,527,970.

U.S. Pat. Nos. 5,849,971 and 5,811,620 disclose processes for dehydration of TBA using reactive distillation. U.S. Pat. No. 5,637,777 discloses a catalytic distillation process for preparing tertiary alkyl ethers from isoolefins. Other processes for preparing tertiary alkyl ethers are disclosed in, for example, U.S. Pat. Nos. 5,292,964, 5,248,836, 5,231,234, and 4,935,552.

Some of the above described processes require additional separation steps which may add significantly to operating and capital expenditures. For example, one-step etherification of TBA may result in the formation of a water-ETBE azeotrope, and water may also form an azeotrope with any unreacted ethanol. The formation of these azeotropes may add to the difficulty and expense of recovering a high purity ETBE product.

Accordingly, there exists a need for an efficient process for the conversion of TBA to ETBE.

SUMMARY OF THE DISCLOSURE

In one aspect, embodiments disclosed herein relate to a process for the conversion of tertiary butyl alcohol to ethyl tertiary butyl ether. The process may include: dehydrating tertiary butyl alcohol to form a product stream comprising isobutylene and water; separating the product stream to form an isobutylene-rich fraction and a water-rich fraction; separating the water-rich fraction to recover a hydrocarbon fraction and a water fraction having less than 1 ppm hydrocarbon content; reacting isobutylene in the isobutylene-rich fraction with ethanol to form a reaction product comprising ethyl tertiary butyl ether; separating the reaction product to recover unreacted ethanol and an ethyl tertiary butyl ether stream; and recycling at least a portion of the unreacted ethanol to the reacting; wherein the ethyl tertiary butyl ether stream comprises at least 99 weight percent ethyl tertiary butyl ether.

In another aspect, embodiments disclosed herein relate to a process for the conversion of tertiary butyl alcohol to ethyl tertiary butyl ether, the process including: feeding a hydrocarbon stream comprising tertiary butyl alcohol to a dehydration reactor; contacting the tertiary butyl alcohol with a dehydration catalyst in the dehydration reactor to dehydrate at least a portion of the tertiary butyl alcohol to form a first reaction product comprising water and isobutylene; separating the first reaction product to form a water-rich phase and an isobutylene-rich phase; treating the water-rich phase to recover residual hydrocarbons and to produce a water-rich phase of reduced hydrocarbon content; feeding the isobutylene and ethanol to a down flow boiling point etherification reactor; passing the isobutylene and the ethanol over an etherification catalyst in the down flow boiling point etherification reactor to react at least a portion of the isobutylene and ethanol to form a vapor/liquid reaction product comprising ethyl tertiary butyl ether; operating the down flow boiling point etherification reactor at a boiling point of the isobutylene, ethanol, and ethyl tertiary butyl ether mixture; recycling at least a portion of the vapor/liquid reaction product to the etherification reactor; separating at least a portion of the vapor/liquid reaction product to form an ethanol-rich phase and ethyl tertiary butyl ether; feeding the ethylene-rich phase to the down flow boiling point etherification reactor.

In another aspect, embodiments disclosed herein relate to a system for the conversion of tertiary butyl alcohol to ethyl tertiary butyl ether, the system including: a first fluid conduit for feeding a hydrocarbon stream comprising tertiary butyl alcohol to a dehydration reactor; a dehydration catalyst in the dehydration reactor to dehydrate at least a portion of the tertiary butyl alcohol to form a first reaction product comprising water and isobutylene; a first separator for separating the first reaction product to form a water-rich phase and an isobutylene-rich phase; a treater for treating the water-rich phase to recover residual hydrocarbons and to produce a water-rich phase of reduced hydrocarbon content; a second fluid conduit for feeding the isobutylene-rich phase and ethanol to a down flow boiling point etherification reactor; a third fluid conduit for feeding ethanol to the down flow boiling point etherification reactor; an etherification catalyst in the down flow boiling point etherification reactor to react at least a portion of the isobutylene and ethanol to form a vapor/liquid reaction product comprising ethyl tertiary butyl ether; a fourth fluid conduit for recycling at least a portion of the vapor/liquid reaction product to the etherification reactor; a second separator for separating at least a portion of the vapor/liquid reaction product to form an ethanol-rich phase and ethyl tertiary butyl ether; a fifth fluid conduit for feeding the ethylene-rich phase to the down flow boiling point etherification reactor.

Other aspects and advantages will be apparent from the following description and the appended claims.

DETAILED DESCRIPTION

Figure 1:
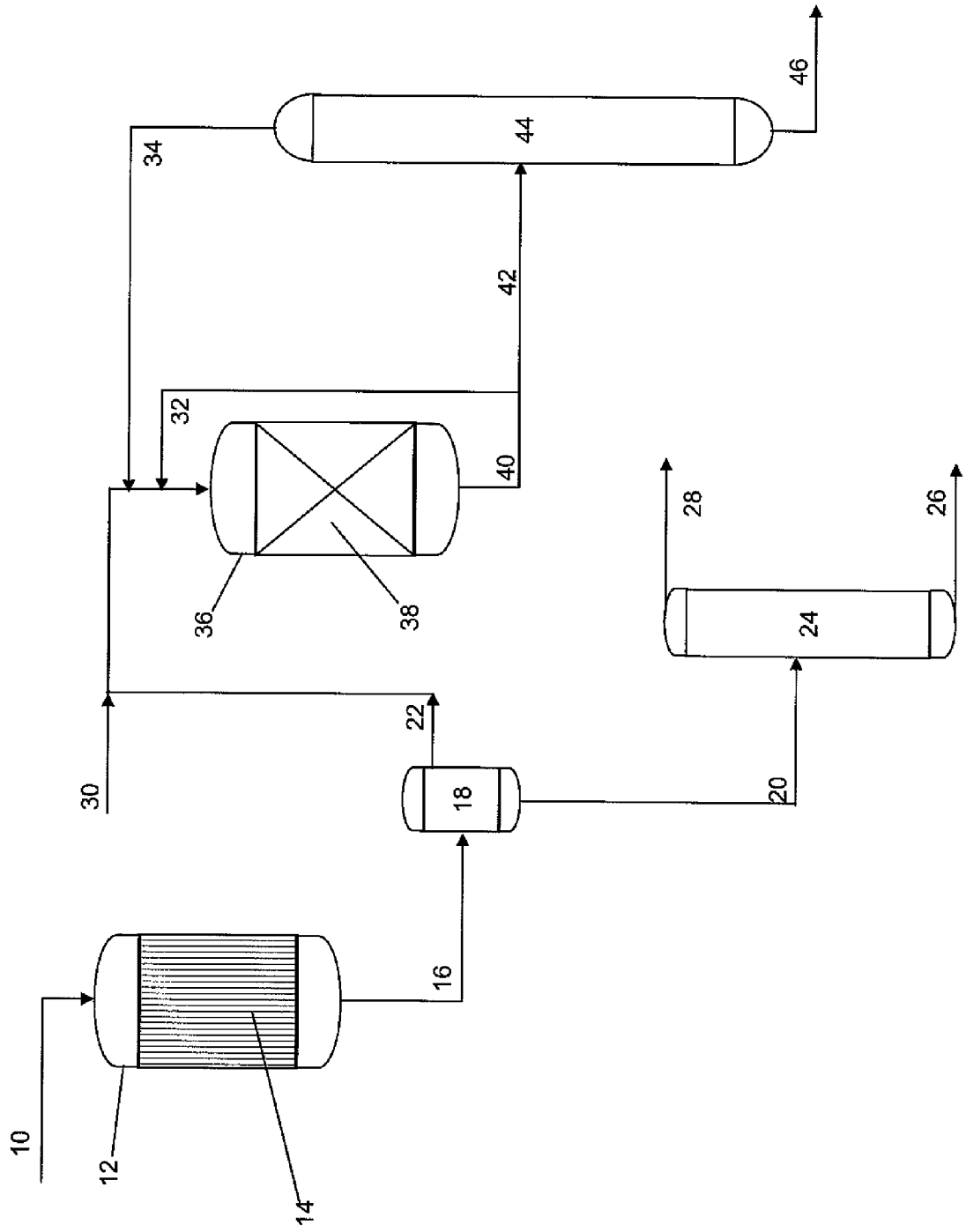
FIG. 1 is a simplified process flow diagram of a process for the conversion of tertiary butyl alcohol to ethyl tertiary butyl ether according to embodiments disclosed herein.

In one aspect, embodiments disclosed herein relate to a process for the conversion of tertiary butyl alcohol (TBA) to ethyl tertiary butyl ether (ETBE). In other aspects, embodiments disclosed herein relate to an energy efficient, heat integrated process and apparatus for the conversion of TBA to ETBE.

Conversion of TBA to ETBE may be performed in a two-step reaction scheme. In a first step, the TBA may be dehydrated to form isobutylene and water. The isobutylene may then be subsequently reacted with ethanol to form ETBE. The reactions may be illustrated as follows:

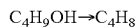

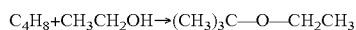

A process for the conversion of tertiary butyl alcohol to ethyl tertiary butyl ether, according to embodiments disclosed herein, may include: dehydrating TBA to form a product stream comprising isobutylene and water; separating the product stream to form an isobutylene-rich fraction and a water-rich fraction; separating the water-rich fraction to recover a hydrocarbon fraction and a water fraction; reacting isobutylene in the isobutylene-rich fraction with ethanol to form a reaction product comprising ethyl tertiary butyl ether; separating the reaction product to recover unreacted ethanol and an ethyl tertiary butyl ether stream; and recycling at least a portion of the unreacted ethanol to the reacting.

Dehydration of TBA may be carried out, for example, in a tubular fixed bed reactor that uses high pressure steam or other heat transfer fluids to effect a temperature ranging from 200 to 800° F. In some embodiments, reaction temperatures may range from 400 to 600° F.; from 420 to 460° F. in other embodiments; and from 430 to 440° F. in yet other embodiments. In other embodiments, reaction temperatures may range from 200 to 400° F.; from 250 to 350° F. in other embodiments; and from 310 to 330° F. in yet other embodiments. Reaction pressures may range from 14 to 115 psia in some embodiments.

The dehydration reaction may be catalyzed by any suitable dehydration catalyst. For example, suitable catalysts may include alumina, acidic zeolites such as Y, beta, and ZSM-5, acid-treated clays, metal-exchanged sulfuric acid macroporous ion exchange resins, and solid phosphoric acid, among others.

At the mild reaction conditions described above, TBA may be dehydrated to high conversions. For example, in some embodiments TBA is dehydrated to a conversion of at least 95 weight percent; at least 97 weight percent in other embodiments; at least 98 weight percent in other embodiments; at least 99 weight percent in other embodiments; at least 99.5 weight percent in other embodiments; and at least 99.8 weight percent in yet other embodiments. Due to the high conversion of TBA that may be achieved, separation and recycle of TBA may not be required in some embodiments. Rather, the residual amount of TBA may be passed to the etherification reaction zone along with the isobutylene formed during the dehydration reaction.

Dehydration reaction products may include water, isobutylene, and unreacted TBA. The hydrocarbons may be separated from the water to result in a water-rich phase and an isobutylene-rich phase. The water-rich fraction may be subsequently treated to remove any residual hydrocarbons, including TBA. In some embodiments, the resulting treated water fraction may have less than 5 ppm hydrocarbon; less than 1 ppm hydrocarbon in other embodiments; and less than 0.5 ppm hydrocarbon in yet other embodiments.

The isobutylene-rich fraction may be mixed with ethanol, which may be from a biological or petrochemical origin, and an ETBE containing diluent. The isobutylene and ethanol in the resulting mixture may be reacted over a suitable etherification catalyst to form ETBE. For example, the mixture may be contacted with a sulfuric acid macroporous ion exchange resin proton form in a suitable reactor to react ethanol and isobutylene to form ETBE with high selectivity to ETBE and low yield to isobutylene dimer. Other suitable etherification catalysts are described in, for example, U.S. Pat. Nos. 5,190,730, 5,231,234, 5,248,836, 5,292,964, 5,637,777, and 6,107,526, among others. Etherification reaction conditions may include, for example, a temperature ranging from 140 to 220° F. in some embodiments; from 150 to 180° F. in other embodiments; and from 160 to 170° F. in yet other embodiments, where the pressure may range from 5 to 50 psig in some embodiments, and from 15 to 25 psig in other embodiments.

The etherification reactor effluent includes isobutylene, ethanol, and ETBE. ETBE and ethanol form a light boiling azeotrope, which may prevent the total separation of ethanol from ETBE in a single distillation tower. However, when a downflow boiling point reactor is used, for example, at least a portion of the reactor effluent may be recycled to provide the ETBE containing diluent and reactor temperature control, allowing ethanol to be recovered with ETBE without a significant penalty. Relative to net etherification reactor feed, the ratio of reactor effluent to net feed may range from 0.5 to 3 in some embodiments, with a preferred value of about 1.

The remaining fraction of the reactor effluent, the portion not used as recycle, may be fractionated in a recovery column to separate the ETBE, recovered as a bottoms fraction, from unreacted isobutylene and ethanol, recovered as an overheads fraction. Due to the azeotrope, some ETBE may remain with the ethanol. The recovered overheads fraction may also be recycled to the etherification reactor. The ratio of the recovery column overhead to net etherification reactor feed may range from about 0.5 to about 5 in some embodiments, from about 1 to about 1.5 in other embodiments, and from 1.2 to 1.4, such as about 1.3, in yet other embodiments.

The resulting ETBE bottoms fraction may have a high purity. For example, the recovered ETBE fraction may have an ETBE content greater than 90 weight percent. In other embodiments, the ETBE fraction may have an ETBE content of greater than 95 weight percent; greater than 97 weight percent in other embodiments; greater than 98 weight percent in other embodiments; greater than 98.5 weight percent in other embodiments; greater than 99 weight percent in other embodiments; greater than 99.1 weight percent in other embodiments; and greater than 99.5 weight percent in yet other embodiments. In other embodiments, the recovered ETBE fraction may have an ethanol content of less than 5000 ppm; less than 2500 ppm in other embodiments; less than 1000 ppm in other embodiments; and less than 500 ppm in yet other embodiments.

Referring now to FIG. 1, a simplified process flow diagram of a process for converting TBA to ETBE, according to embodiments disclosed herein, is illustrated. TBA may be fed via line 10 to a dehydration reactor 12. Dehydration reactor 12 may include a dehydration reaction zone 14 containing a suitable dehydration catalyst, such as those described above. Contact of TBA with the dehydration catalyst at appropriate reaction conditions may result in the dehydration of TBA to form isobutylene and water, which may be recovered via line 16.

The recovered water and isobutylene in line 16 may then be fed to a separator 18, such as a decanter, a flash separator, an oil/water separator, a coalescer, or other suitable oil/water separation devices. Separator 18 may allow for the separation of the water and isobutylene, forming a water-rich fraction, which may be recovered via line 20, and an isobutylene rich fraction, which may be recovered via line 22.

The recovered water-rich fraction in line 20 may be further treated to separate any residual hydrocarbons from the water in separator 24, such as an oil/water separator, a coalescer, or a clarifier, among other oil/water separation devices. Separator 20 may result in water suitable for biological treatment, having a low hydrocarbon concentration, as described above. The water having a low hydrocarbon content may be recovered via line 26, and the hydrocarbons, including TBA, may be recovered via line 28.

The recovered isobutylene-rich fraction in line 22 may be combined with ethanol, fed via line 30, and optionally ETBE recycle, fed via line 32, and ethanol recycle, fed via line 34. The resulting mixture may be fed to etherification reactor 36, which may include an etherification reaction zone 38 containing a suitable etherification catalyst, such as those described above. Contact of isobutylene and ethanol over the etherification catalyst at appropriate reaction conditions may result in the reaction of ethanol and isobutylene to form ETBE. The reaction product, which may include unreacted isobutylene and ethanol, may be recovered via line 40. A portion of the reaction product may be recycled via line 32, and the portion not recycled may be fed via line 42 to distillation column 44 to effect the separation of unreacted ethanol and isobutylene, which may be recovered as an overheads fraction via line 34 and recycled to the top of the etherification reactor 36, and the ETBE, which may be recovered as a bottoms fraction via line 46.

Etherification reactor 36 may be a down flow boiling point reactor. In some embodiments, the down flow boiling point reactor may be operated in the pulse flow regime. The pulses may be characterized by large mass and heat transfer rates. Increased catalyst/contact structure wetting and a continuous mixing between parallel flowing rivulets may diminish flow maldistribution. In addition, the formation of local hot spots may be reduced, leading to an intrinsically safer process. The pulses may continuously mobilize stagnant liquid holdup to the point where its stagnant nature disappears. Since stagnant holdup represents 10 to 30 percent of the total liquid holdup in trickle flow operations, the dynamic character of the pulse flow regime may enhance reactor performance, such as by improved radial mixing.

The energy efficiency of the above describe TBA conversion process may be improved through the recovery of heat from the dehydration reactor outlet stream and the esterification reactor outlet stream. For example, heat may be recovered from the dehydration reaction product through indirect heat exchange with at least one of the tertiary butyl alcohol feed and at least a portion of the esterification reaction product prior to entering the distillation column for separations. As another example, heat may be recovered from the esterification reaction product stream through indirect heat exchange with at least one of the ethanol recycle stream, the distillation column overhead fraction, and a cooled portion of the esterification reaction product stream. Heat may also be recovered from the distillation column bottoms through indirect heat exchange with the distillation column feed.

Figure 2:
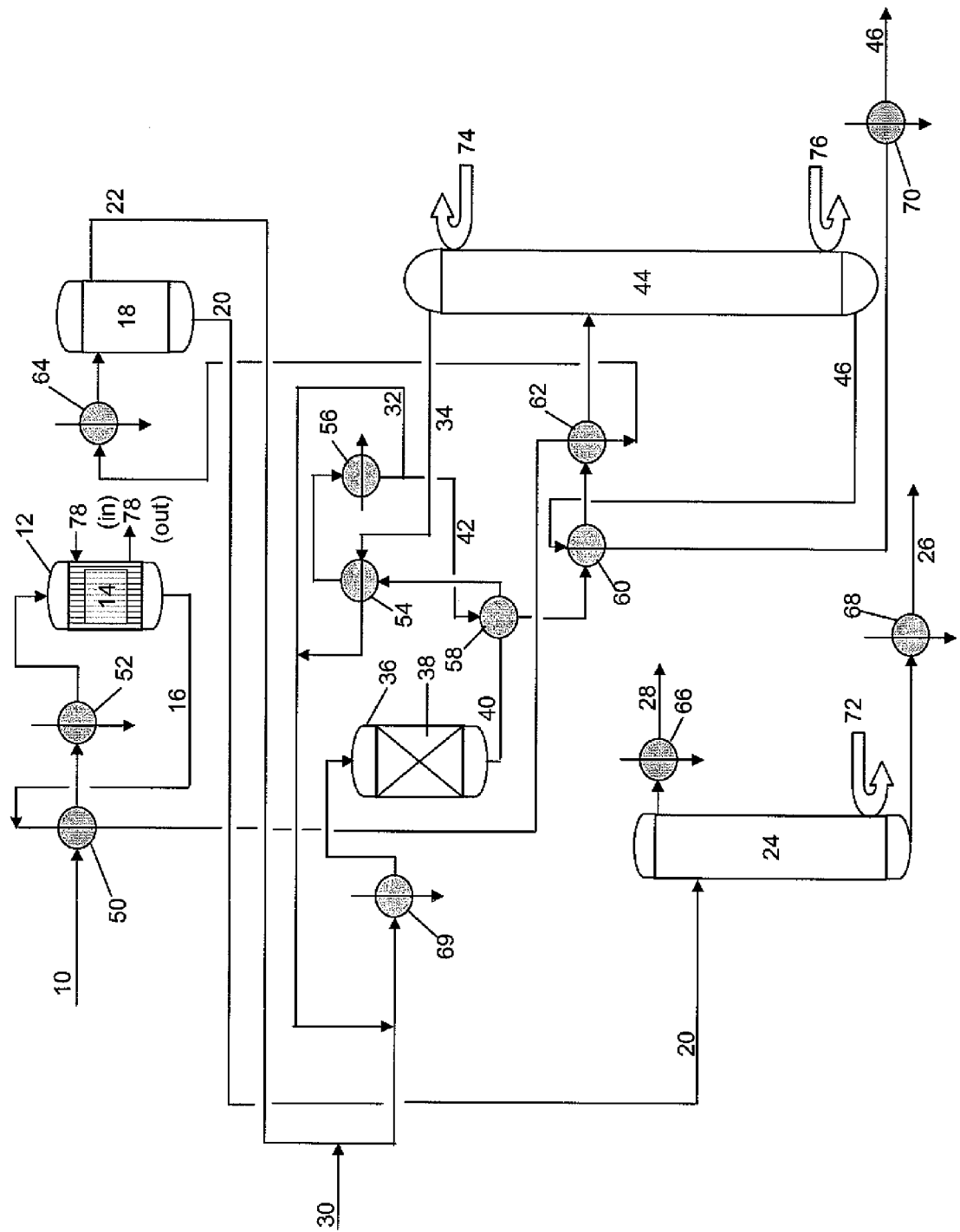
FIG. 2 is a simplified process flow diagram of a process for the conversion of tertiary butyl alcohol to ethyl tertiary butyl ether, including a heat exchange network, according to embodiments disclosed herein.

Referring to FIG. 2, where like numerals represent like parts, a simplified process flow diagram of an energy efficient process for the conversion of tertiary butyl alcohol to ethyl tertiary butyl ether, according to embodiments disclosed herein, is illustrated. The general flow scheme is similar to that as illustrated in FIG. 1. In this embodiment, one possible flow scheme for the recapture of heat from various process streams is illustrated. Other heat exchange networks are also possible, but will not be described herein.

As illustrated in FIG. 2, prior to entering the dehydration reactor, the TBA feed in line 10 may be preheated. In some embodiments, the TBA feed may be preheated through indirect heat exchange with the dehydration reaction product stream, such as that recovered via line 16, in heat exchanger 50. The TBA stream 10 may also be preheated through indirect heat exchange in one or more heat exchangers 52.

A second heat exchange network may be used to recover heat from the esterification reactor product stream 40 and the distillation column 44 bottoms fraction 46. For example, the esterification reactor product stream 40 may be used to heat the distillation column overheads fraction 34 in heat exchanger 54. If needed, a heat exchanger 56 may be used to further cool esterification reactor product stream 40 prior to division into ETBE diluent recycle stream 32 and distillation column feed stream 42. Distillation column feed stream 42 may be heated prior to entering distillation column 44 using one or more of the esterification reactor product stream 40, distillation column bottoms fraction 46, and dehydration reactor product stream 16, such as by using indirect heat exchangers 58, 60, and 62, respectively. Additional heat exchangers may be used to cool the feed and product streams as needed, a few of which are illustrated as heat exchangers 64, 66, 68, 69, and 70. Additional heating and cooling may also be required for the system, such as heat input 72, adding heat to improve separations achieved in separator 24, distillation column reboiler heat input 74, distillation column overhead system cooling 76, and heating fluid 78, controlling temperature of the dehydration reactor. Although illustrated as concurrent flow, steam or other heating fluids 78 may be used in countercurrent flow in reactor 12.

EXAMPLE

TBA is converted to ETBE in a process similar to that described above for FIG. 2. TBA is fed to the dehydration reactor at a rate of 11,000 barrels per day (125748 lb/h; 57038 kg/h), and fresh ethanol is fed at a rate of 6747 barrels per day (77211 lb/h; 35022 kg/h). The TBA dehydration reactor 14 was operated at a temperature ranging from 430 to 440° F., with no recycle. The etherification reactor 38 was operated at a temperature ranging from 160 to 170° F., and an operating pressure between 15 and 25 psig. The ratio of etherification reactor effluent (stream 32) to net feed (stream 22) was approximately 1, and the ratio of recovery column 44 overheads (stream 34) to net reactor feed (stream 22) was approximately 1.3.

Operation of the process as described above results in the production of approximately 16382 barrels per day of ETBE (172761 lb/h; 78363 kg/h) having a purity of approximately 99.15 weight percent and approximately 1000 ppm of ethanol. The water-rich fraction is separated to result in approximately 2081 barrels per day (30108 lb/h; 13657 kg/h) water having less than 1 ppm hydrocarbons and the recovery of approximately 214 lb/h (97 kg/h) hydrocarbon.

Utility requirements for the above process are approximately 71600 lb/h (32477 kg/h) high pressure steam (425 psig or higher), 93700 lb/h (42502 kg/h) medium pressure steam (150 psig or higher), 4600 lb/h (2087 kg/h) low pressure steam (approximately 20 psig), 392200 gallons per hour cooling water, and approximately 200 kW electrical power.

As described above, embodiments disclosed herein may provide for the conversion of TBA to result in a high purity ETBE. Advantageously, embodiments disclosed herein may provide for the realization of a higher value product from the TBA resulting from a propylene oxide production process. Other embodiments disclosed herein may provide for an energy efficient process for conversion of TBA to TBE through use of heat exchange networks, recovering excess heat from various process streams.

While the disclosure includes a limited number of embodiments, those skilled in the art, having benefit of this disclosure, will appreciate that other embodiments may be devised which do not depart from the scope of the present disclosure. Accordingly, the scope should be limited only by the attached claims.

What is claimed:

1. A process for the conversion of tertiary butyl alcohol to ethyl tertiary butyl ether, the process comprising:
    feeding a hydrocarbon stream comprising tertiary butyl alcohol to a dehydration reactor;
    contacting the tertiary butyl alcohol with a dehydration catalyst in the dehydration reactor to dehydrate at least a portion of the tertiary butyl alcohol to form a first reaction product comprising water and isobutylene;
    separating the first reaction product to form a water-rich phase and an isobutylene-rich phase;
    treating the water-rich phase to recover residual hydrocarbons and to produce a water-rich phase of reduced hydrocarbon content;
    feeding the isobutylene and ethanol to a down flow boiling point etherification reactor;
    passing the isobutylene and the ethanol over an etherification catalyst in the down flow boiling point etherification reactor to react at least a portion of the isobutylene and ethanol to form a vapor/liquid reaction product comprising ethyl tertiary butyl ether;
    operating the down flow boiling point etherification reactor at a boiling point of the isobutylene, ethanol, and ethyl tertiary butyl ether mixture;
    recycling at least a portion of the vapor/liquid reaction product to the etherification reactor;
    separating at least a portion of the vapor/liquid reaction product to form an ethanol-rich phase and ethyl tertiary butyl ether;
    feeding the ethanol-rich phase to the down flow boiling point etherification reactor.

2. The process of claim 1, further comprising recovering heat from the first reaction product through heat exchange with at least one of the tertiary butyl alcohol feed and a portion of the vapor/liquid product stream.

3. The process of claim 2, further comprising recovering heat from the vapor/liquid product stream through heat exchange with at least one of the ethanol-rich stream, the ethanol, and a cooled portion of the vapor/liquid product stream.

4. The process of claim 3, further comprising recovering heat from the ethyl tertiary butyl ether through heat exchange with a portion of the vapor/liquid product stream.

5. The process of claim 1, wherein the recycling comprises returning a sufficient portion of the vapor/liquid reaction product to the etherification reactor to maintain a fully wetted etherification catalyst.

6. A system for the conversion of tertiary butyl alcohol to ethyl tertiary butyl ether, the system comprising:
    a first fluid conduit for feeding a hydrocarbon stream comprising tertiary butyl alcohol to a dehydration reactor;
    a dehydration catalyst in the dehydration reactor to dehydrate at least a portion of the tertiary butyl alcohol to form a first reaction product comprising water and isobutylene;
    a first separator for separating the first reaction product to form a water-rich phase and an isobutylene-rich phase;
    a treater for treating the water-rich phase to recover residual hydrocarbons and to produce a water-rich phase of reduced hydrocarbon content;
    a second fluid conduit for feeding the isobutylene-rich phase and ethanol to a down flow boiling point etherification reactor;
    a third fluid conduit for feeding ethanol to the down flow boiling point etherification reactor;
    an etherification catalyst in the down flow boiling point etherification reactor to react at least a portion of the isobutylene and ethanol to form a vapor/liquid reaction product comprising ethyl tertiary butyl ether;
    a fourth fluid conduit for recycling at least a portion of the vapor/liquid reaction product to the etherification reactor;
    a second separator for separating at least a portion of the vapor/liquid reaction product to form an ethanol-rich phase and ethyl tertiary butyl ether;
    a fifth fluid conduit for feeding the ethanol-rich phase to the down flow boiling point etherification reactor.

7. The system of claim 6, further comprising a heat exchange network for recovery of at least a portion of heat from the first reaction product.

8. The system of claim 6, further comprising a heat exchange network for recovery of at least a portion of heat from the vapor/liquid reaction product.

* * * * *